(12) United States Patent
Rombach et al.

(10) Patent No.: US 12,721,723 B2
(45) Date of Patent: Sep. 1, 2026

(54) COMBINATION OF LENS HOLDER AND LENS INJECTOR CARTRIDGE FOR INTRAOCULAR LENS WITH MULTIPLE OPTICAL ELEMENTS

(71) Applicant: AKKOLENS INTERNATIONAL B.V., Breda (NL)

(72) Inventors: Michiel Christiaan Rombach, Breda (NL); Willem Pieter Van Lawick, Breda (NL)

(73) Assignee: AKKOLENS INTERNATIONAL B.V., Breda (NL)

( * ) Notice: Subject to any disclaimer, the term of this patent is extended or adjusted under 35 U.S.C. 154(b) by 1092 days.

(21) Appl. No.: 17/568,867

(22) Filed: Jan. 5, 2022

(65) Prior Publication Data

US 2022/0211490 A1 Jul. 7, 2022

(30) Foreign Application Priority Data

Jan. 5, 2021 (NL) ..................................... 2027268

(51) Int. Cl.
*A61F 2/16* (2006.01)

(52) U.S. Cl.
CPC .......... *A61F 2/1678* (2013.01); *A61F 2/1691* (2013.01); *A61F 2/1648* (2013.01); *A61F 2240/001* (2013.01)

(58) Field of Classification Search
CPC .................. A61F 2/1678; A61F 2/1691; A61F 2240/001; A61F 2/1662; A61F 2/1648
See application file for complete search history.

(56) References Cited

U.S. PATENT DOCUMENTS 6,129,733 A * 10/2000 Brady ................... A61F 2/1691 606/107
9,713,526 B2 7/2017 Rombach
2005/0049605 A1* 3/2005 Vaquero ................ A61F 2/1678 606/107
2006/0037871 A1* 2/2006 Jin ........................ A61F 2/1691 206/5.1
2008/0039862 A1* 2/2008 Tran ...................... A61F 2/1662 606/107
2008/0097598 A1* 4/2008 Engin .................. A61F 2/1648 623/6.12
2012/0165824 A1* 6/2012 Tsai ...................... A61F 2/1648 606/107
2015/0342728 A1 12/2015 Simonov et al.

FOREIGN PATENT DOCUMENTS

NL 2012031 A 7/2014
NL 2023333 A 1/2020
WO 2005084587 A3 9/2005
WO WO-2007037689 A2 * 4/2007 ........... A61F 2/1691

* cited by examiner

*Primary Examiner* — Javier G Blanco
(74) *Attorney, Agent, or Firm* — The Webb Law Firm

(57) ABSTRACT

The present invention relates to a combination of an intraocular lens, a lens holder and a lens injector cartridge for the intraocular. The lens holder is provided with a connector, to couple the lens holder to the lens injector cartridge or the lens holder is integrally formed with the lens injector cartridge. The lens injector cartridge includes a loading chamber to receive the intraocular lens. The lens holder includes a spacer, where the spacer is configured to be coupled to the intraocular lens and where the spacer separates at least two optics of the intraocular lens.

7 Claims, 4 Drawing Sheets

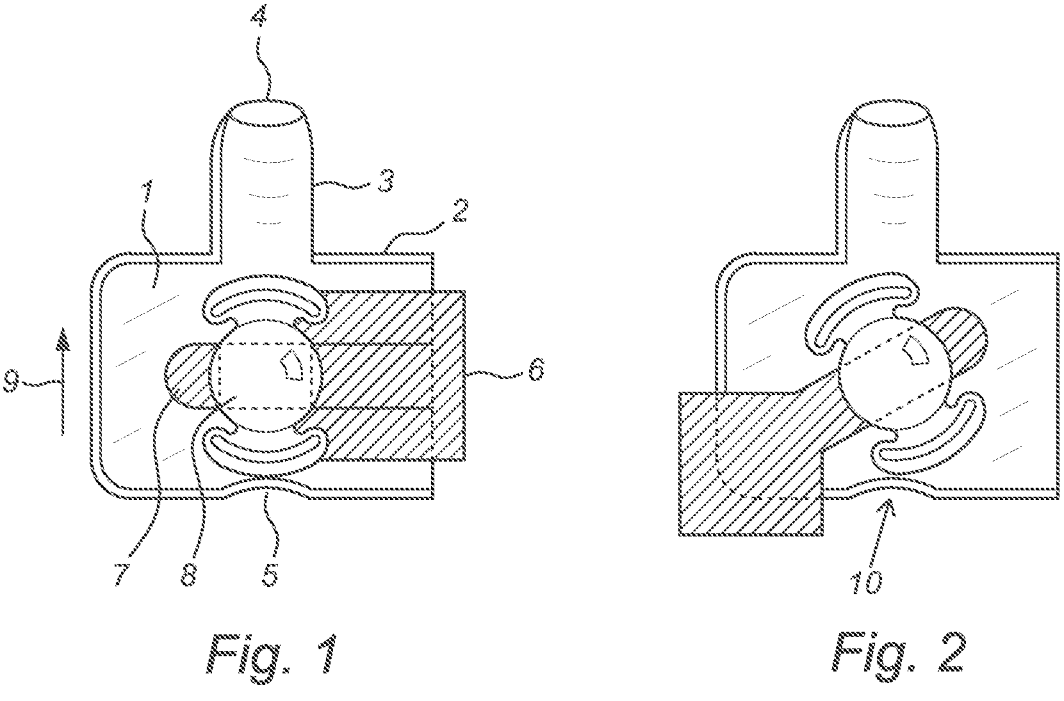
Fig. 1
Fig. 2
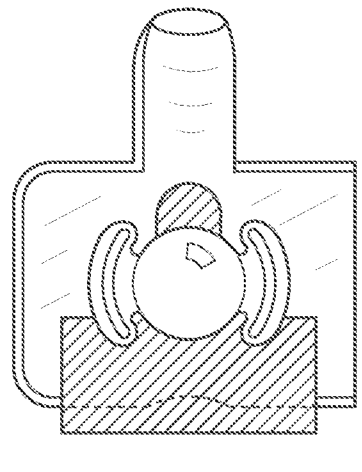
Fig. 3
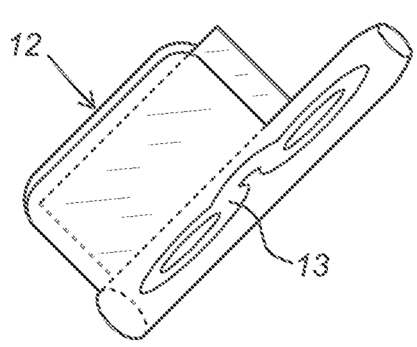
Fig. 4

16
21
20
19
17
15
69
14
18
22

25
23
26
24
27

29
28
32
30
34
31
33

38
35
41
42
36
37
39
40

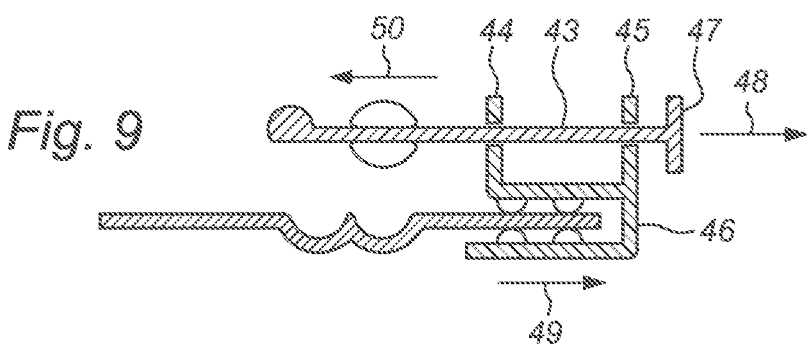
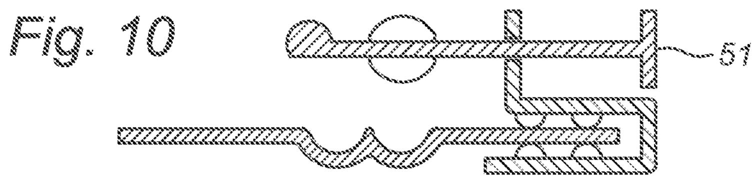
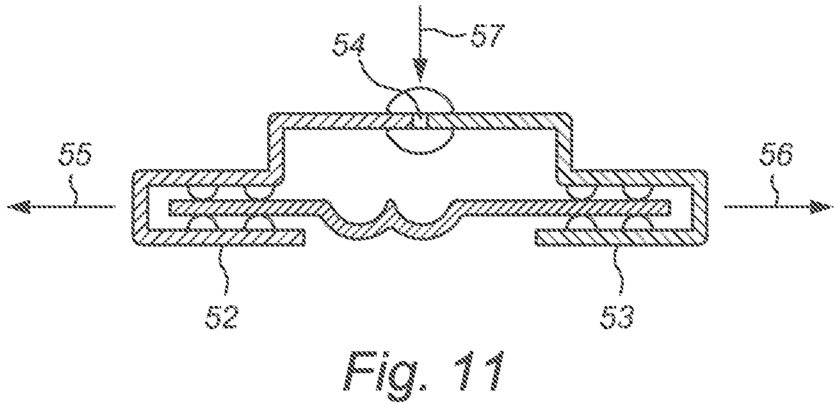
Fig. 11
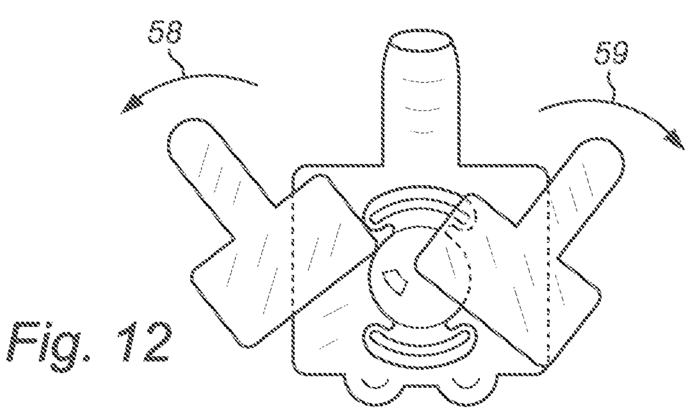
Fig. 12

COMBINATION OF LENS HOLDER AND LENS INJECTOR CARTRIDGE FOR INTRAOCULAR LENS WITH MULTIPLE OPTICAL ELEMENTS

CROSS-REFERENCE TO RELATED APPLICATION

This application claims priority to The Netherlands Patent Application No. 2027268 filed Jan. 5, 2021, the disclosure of which is hereby incorporated by reference in its entirety.

BACKGROUND OF THE INVENTION

Field of the Invention

This document discloses a combination of intraocular lens holder for lens with multiple optical elements and lens injector butterfly cartridge. The combination ensures proper positioning of the lens in cartridge during surgery, separation of optical elements and separation of the lens and cartridge during sterilization, transport and storage. The lens holder comprises a primary spacer component for separation of the optical elements and a secondary spacer to separate the posterior optical element of the lens from the cartridge. Additional lens holder components include coupling components to connect lens holder and cartridge, swiper components to deliver the lens from the holder onto the loading chamber of the cartridge and components for coupling the combination into packaging.

Description of Related Art

Intraocular lenses do generally not have a preferred implantation position, meaning: do not have, once in the eye, a preferred front, anterior, and back, posterior, side. However, accommodating intraocular lenses comprising two optical elements as disclosed in, for example, WO2005084587, NL2023333, US2015342728 and multiple related documents have a preferred front and backside. With such lenses separation of the optical elements during manufacturing, sterilization, transport and storage should be achieved to prevent, for example, sticking of optical element surfaces during sterilization as well as prevention of upside/down implantation in the eye. A first generation of a lens holder to do such is disclosed in NL2012031. The present document discloses a second generation of such a lens holder in combination with a lens injector cartridge. The holder ensures spacing of the optical elements, spacing of the posterior surface of the lens and the cartridge and ensures prevention of accidental inversion of the lens, accidental upside-down loading, during the loading procedure of the lens into the cartridge.

SUMMARY OF THE INVENTION

The present document discloses a combination of a lens holder and lens injector cartridge for a, multiple optical component, accommodating intraocular lens which ensures prevention of upside down implantation into the eye. The combination provides alignment of the lens with the loading chamber of the cartridge, for example, a butterfly cartridge, by at least one primary spacer component coupled to the lens, separation of the optical components by the primary spacer component and separation of the posterior surface of the lens and the anterior surface of the cartridge by at least one secondary spacer component during sterilization, transport and storage of the lens. The primary spacer component is, preferably, but not restricted hereto, positioned largely parallel to the wings of the butterfly cartridge with the secondary spacer element being positioned largely perpendicular to the butterfly wings.

So, the combination of a lens, a lens holder and a lens injector cartridge for an intraocular lens with multiple optical components, with, (a) the lens holder provided with coupling means, to couple the lens holder to the lens injector cartridge or wherein the lens holder is integrally formed with the lens injector cartridge and, (b) with the lens injector cartridge comprising a loading chamber to receive the lens and, (c) the lens holder comprising a primary spacer component, wherein the primary spacer component is to be coupled to the lens and/or wherein the primary spacer component separates at least two optical components of the intraocular lens and, (d) with the lens holder optionally comprising a secondary spacer component, for separating a posterior surface of the lens and an anterior surface of the lens injector cartridge.

BRIEF DESCRIPTION OF THE DRAWINGS

The invention will be elucidated on the basis of non-limitative exemplary embodiments shown in the following figures, wherein:

FIG. 1 shows a top view of an opened butterfly cartridge according to the invention, wherein the lens is positioned and aligned parallel with the loading chamber of the cartridge;

FIG. 2 shows a top view of an opened butterfly cartridge according to the invention, wherein the lens is positioned and aligned at an angle with the loading chamber of the cartridge;

FIG. 3 shows a top view of an opened butterfly cartridge according to the invention, wherein the lens is positioned perpendicular with the loading chamber of the cartridge;

FIG. 4 shows a top view of a closed butterfly cartridge with a lens folded in the loading chamber;

FIGS. 9 and 10 show an embodiment of a spacer-swiper component according to the invention;

FIGS. 11 and 12 show an embodiment of a lens holder with two identical lens holders according to the present invention;

DESCRIPTION OF THE INVENTION

FIGS. 1-4 shows a top view of an, opened, butterfly cartridge with the cartridge wings, 1,2, the cartridge sprout, 3, the cartridge exit opening, 4, the cartridge loading chamber, 5, and the lens holder, 6, with the attached lens spacer component, 7, and an accommodating intraocular lens, 8, in this example, as disclosed in, NL202333, mounted on the lens spacer component. FIG. 1 shows an embodiment of the combination the lens is positioned in a direction parallel, 9, aligned to the loading chamber of the cartridge with FIG. 2 showing an embodiment of the combination with the lens is positioned in a direction aligned at an angle, 10, to the loading chamber of the cartridge, also referred to as a 'Z-loading' position, with FIG. 3 showing an embodiment of the combination with the lens is positioned in a direction perpendicular, 11, to the loading chamber of the cartridge and with FIG. 4 showing the butterfly cartridge in a closed configuration, 12, with the lens, 13, folded into the loading chamber and ready for injection into the eye when pushed by the plunger of the lens injector.

Figures 5, 6, 7, 8:
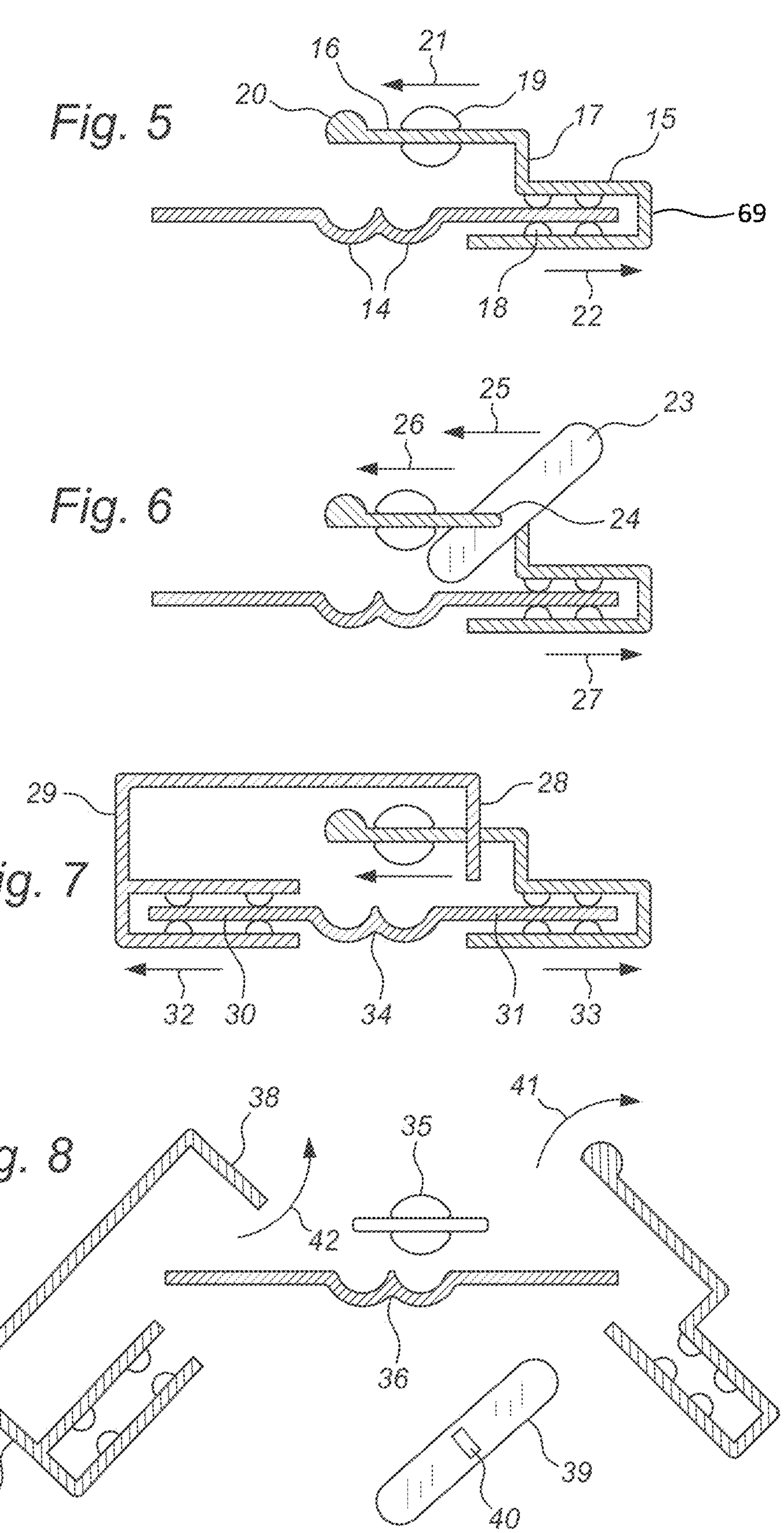
FIG. 5 shows a backside view of a cartridge according to the invention in opened position.
FIG. 6 shows the embodiment of FIG. 5 with a swiper component.
FIG. 7 shows the embodiments of FIGS. 5 and 6, with a swiper holder component.
FIG. 8 shows the components of the FIG. 7 embodiment individually.

FIGS. 5-6 show embodiments of the combination from the backside view of the cartridge which, in opened positioned, shows the two halves of the loading chamber, 14, the lens holder, 15, comprising the primary spacer component, 16, which separates the two optical elements of the lens and the secondary spacer component, 17, which separates the posterior surface of the lens from the cartridge, with the holder having clipping component, 69, such that the holder is clipped/folded around a wing of the cartridge, with the holder being held in place by a coupling means, 18, with the lens, 19, mounted on the primary spacer component and with the primary spacer component fitted with a ridge, 20, which ridge provides prevention of the lens accidentally slipping of the spacer component during sterilization, or transport or storage. In this example, the coupling means, 18, is a double pin-in-hole/pin-in-dimple construction. The arrow, 21, shows the direction in which the lens is swiped of the spacer component during surgery and the arrow, 22, the direction in which the lens holder is removed from the lens cartridge following deposition of the lens on top of the loading chamber and with FIG. 6 showing an embodiment as in FIG. 5 to which a swiper component, 23, comprising a slit, 24, through which the lens spacer component is protruding is added. Swiper of the lens in the direction of the arrow, 25, moves the lens in the direction of the arrow, 26, and deposits the lens in the correct position onto the loading chamber which swiper is followed by removal/de-coupling of the lens holder from the cartridge in the direction of the arrow, 27.

FIGS. 7-8 show an embodiment which comprises a swiper component, 28, attached to a swiper holder component, 29, which component is reversibly coupled to the other wing, 30, compared to the wing, 31, to which the lens holder is coupled. Pulling the swiper holder component and the lens holder in opposite directions, 32, 33, will deposit the lens in the correct position onto the loading chamber of the cartridge, 34, with FIG. 8 showing the various components of the combination as in FIG. 7 following deposition of the lens onto the cartridge loading chamber with the components including the lens, 35, onto the loading chamber, 36 and the swiper holder component, 37, comprising the swiper, 38. Or, alternatively, in an embodiment according to FIG. 6, the lens, 35, onto the loading chamber, 36, the lens holder and the, independent, swiper component, 39, comprising the slit, 40.

The arrows 41, 42, indicate the directions in which the lens holder and the swiper holder component can be removed/de-coupled from the cartridge.

FIGS. 9-10 show a primary spacer-swiper component, 43, positioned through a slit into the secondary spacer component, 44, with the primary spacer-swiper component also supported by an additional supporting component, 45, fixed to the lens holder, 46. In this example the primary spacer-swiper component comprises also a holding component, 47, to allow easy deposition of the lens onto the loading chamber by pulling the holding component into the direction of the arrow, 48, after which the lens holder can be removed/de-coupled by pulling the holder in the direction of the arrow, 49. The lens slips into the direction of the arrow, 50, for deposition onto the loading chamber of the cartridge with FIG. 10 showing an example of a holding component, 51, which also doubles as an additional supporting component as illustrated in FIG. 9.

FIG. 11 and FIG. 12 show an example of a lens holder which comprises two identical lens holders, 52, 53, positioned opposite each other with one lens holder on each wing of the butterfly cartridge with each lens holder comprising a primary lens spacer with the spacers meeting, 54, almost touching, above the loading chamber of the cartridge. The lens holders can either be removed in opposite directions, 55, 56, which deposits the lens onto the loading chamber, or, alternatively, the lens can be mechanically pushed down, 57, by a surgical tool through the hole between the elastic primary spacer components after which the lens holders can be removed/de-coupled from the cartridge with FIG. 12 showing turning movements, 58, 59, which can be applied to remove the lens holders from the cartridge after the lens is deposited onto the cartridge.

Figure 13:
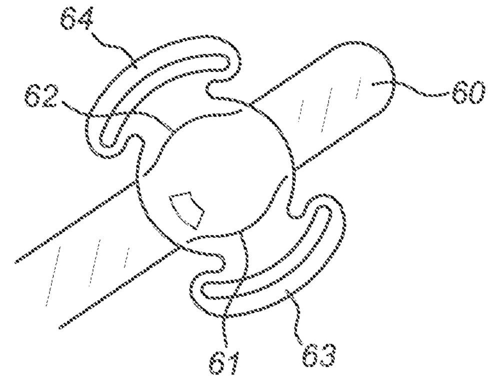
FIG. 13 shows a primary spacer component according to the present invention.

FIG. 13 shows a primary spacer component, 60, comprising primary spacer wing components, 61, 62, which, firstly, provide additional separation of optical surfaces adjacent to the hinges, 63, 64, of the accommodating lens and, secondly, prevent the lens accidentally slipping of the holder before surgery. Such primary spacer wings can be sized according to specifications of a particular lens, for example by 3D printing of customized lens holders.

Figure 14:
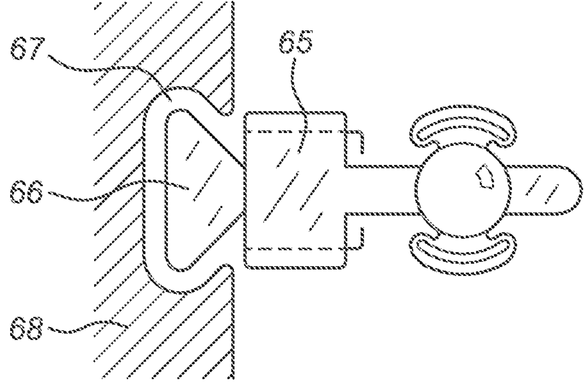
FIG. 14 shows a top view of a lens holder according to the present invention.

FIG. 14 shows a top view of the lens holder, 65, comprising a holder packaging component, 66, to be reversibly coupled to at least one packaging holder component, 67, to provide positioning of the holder into the sterile packaging, 68, during sterilization, transport and storage of the lens with the coupling, in this example, a sliding pin-in-groove connection. Note that the primary spacer component comprises primary spacer wings in this example.

The lens holder comprises at least one clipping component adapted to provide coupling of the lens holder to the cartridge. The coupling may be provided by, for example, a pin-in hole coupling construction.

The holder can comprise at least one swiper component adapted to de-couple the lens from, slipping the lens from, the primary spacer component. Such wiping component can be fixed or reversibly attached to the cartridge or lens holder or, alternatively, be an independent component.

The primary spacer component can comprise at least one terminal holding ridge adapted to prevent slipping of the lens from the spacer by, relatively weak, for example shaking, mechanical forces during sterilization, transport and storage. However, the ridge allows de-coupling of the lens from the spacer by, relatively strong, mechanical forces by the wiping component or surgical mechanical means, for example surgical tweezer or Sinskey hook means. The secondary spacer component prevents contact between the posterior surface of the lens and the cartridge.

The combination can comprise at least one holder packaging component which component is adapted to be reversibly coupled to at least one packaging holder component adapted to provide positioning of the holder into the sterile packaging during sterilization, transport and storage of the lens.

The combination of lens holder and injector cartridge can be assembled during manufacturing, or, alternatively, the combination of lens holder and injector cartridge can be assembled during surgery.

The method for application of the combination assembled during manufacturing includes at least the steps of—opening of the packaging and removing the combination of lens holder and lens injector cartridge from the package, —de-coupling the lens by the wiping component from the spacer component, —removal of the lens holder and wiping component from the cartridge, —closing of the cartridge and insertion of the cartridge into the lens injector, and, —injection of the lens into the eye. Alternatively, the method for application of the combination assembled during surgery includes at least the steps of—opening of packaging and assembly of the lens holder and cartridge into the combination of lens holder and injector cartridge, —de-coupling the lens by the wiping component from the spacer component, —removal of the lens holder and wiping component from the cartridge, —closing of the cartridge and insertion of the cartridge into the lens injector, and, —injection of the lens into the eye.

The lens holder and additional components can be manufactured by traditional injection molding of at least one medically certified polymer, which method allows for inexpensive manufacturing of large volumes of holders, or, alternatively, by 3D printing of at least one medically certified polymer, which method is relatively expensive but allows for customization of each individual holder, or, alternatively, by stamping of at least one medically certified polymer film.

So, in summary, the present document discloses a combination of a lens, a lens holder and a lens injector cartridge for an intraocular lens with multiple optical components. The lens holder is provided with coupling means, to couple the lens holder to the lens injector cartridge or with the lens holder integrally formed with the lens injector cartridge and the lens injector cartridge comprises a loading chamber to receive the lens and the lens holder comprises a spacer component, with the spacer component to be coupled to the lens with the spacer component separating at least two optical components of the intraocular lens.

The combination can comprise a holder comprising at least one clipping component to provide coupling of the lens holder to the cartridge. Also, the holder can comprise at least one swiper component to de-couple the lens from the spacer component.

Furthermore, the lens holder can comprise at least one holder packaging component which component to be reversibly coupled to at least one packaging holder component to provide positioning of the holder into the sterile packaging during sterilization, transport and storage of the lens.

The combination of lens holder and injector cartridge can be assembled during manufacturing, or, alternatively, be assembled at surgery, just prior to lens injection into the eye.

Combination of a lens holder and a lens injector cartridge, to be used in the combination according to any of the preceding claims and suitable to receive a lens in the lens holder.

A method for the combination can include at least the steps of: —opening of the packaging and removing the combination of lens holder and lens injector cartridge from the package, —de-coupling the lens by the wiping component from the spacer component, —removal of the lens holder and wiping component from the cartridge, —closing of the cartridge and insertion of the cartridge into the lens injector, and, optionally, —injection of the lens into the eye. Or, alternatively, a method for the combination can include at least the steps of: —opening of packaging and assembly of the lens holder and cartridge into the combination of lens holder and injector cartridge, —de-coupling the lens by the wiping component from the spacer component, —removal of the lens holder and wiping component from the cartridge, —closing of the cartridge and insertion of the cartridge into the lens injector, and, optionally, —injection of the lens into the eye.

The invention claimed is:

1. A combination of an intraocular lens (IOL), a lens holder sized and configured for holding the intraocular lens, and a lens injector cartridge for the intraocular lens, a. wherein the intraocular lens comprises at least two distinct optics, wherein each optic comprises an optical power;

b. wherein the lens holder is provided with a connector, to couple the lens holder to the lens injector cartridge;

c. wherein the lens injector cartridge comprises a loading chamber to receive the intraocular lens;

d. wherein the lens holder comprises a spacer, wherein the spacer is configured to be coupled to the intraocular lens and wherein the spacer separates the at least two optics of the intraocular lens by forming a physical barrier between the at least two optics.

2. The combination according to claim 1, wherein the lens holder comprises at least one fold, wherein the fold is provided with a second connector.

3. The combination according to claim 1, wherein the lens holder comprises at least one remover adapted to de-couple the intraocular lens from the spacer.

4. The combination according to claim 1, wherein the lens holder comprises at least one holder packaging component, wherein the at least one holder packaging component is adapted to be reversibly coupled to at least one packaging holder component adapted to provide positioning of the lens holder into a sterile packaging during sterilization, transport and storage of the intraocular lens.

5. The combination according to claim 1, wherein the combination of the lens holder and the lens injector cartridge is assembled during manufacturing.

6. The combination according to claim 1, wherein the combination of the lens holder and the lens injector cartridge is assembled at surgery.

7. The combination according to claim 1, wherein the intraocular lens further comprises haptics attached to the optics.

* * * * *